United States Patent
Kolb

(10) Patent No.: US 10,531,904 B2
(45) Date of Patent: Jan. 14, 2020

(54) BONE SCREW WITH APERTURES

(71) Applicant: Eric D. Kolb, Sandy Hook, CT (US)

(72) Inventor: Eric D. Kolb, Sandy Hook, CT (US)

(*) Notice: Subject to any disclaimer, the term of this patent is extended or adjusted under 35 U.S.C. 154(b) by 820 days.

(21) Appl. No.: 14/699,458

(22) Filed: Apr. 29, 2015

(65) Prior Publication Data

US 2015/0313658 A1 Nov. 5, 2015

Related U.S. Application Data

(60) Provisional application No. 61/986,602, filed on Apr. 30, 2014.

(51) Int. Cl.
*A61B 17/86* (2006.01)
*F16B 39/30* (2006.01)
*F16B 33/02* (2006.01)

(52) U.S. Cl.
CPC ........ *A61B 17/8625* (2013.01); *A61B 17/863* (2013.01); *A61B 2017/8655* (2013.01); *A61B 2560/00* (2013.01); *F16B 33/02* (2013.01); *F16B 39/30* (2013.01)

(58) Field of Classification Search
CPC .............. A61B 17/8625; A61B 17/863; A61B 2017/8655; F16B 33/02; F16B 39/30
USPC ....... 606/300, 301, 316, 314, 309, 308, 304; 411/417, 436, 437, 411
See application file for complete search history.

(56) References Cited

U.S. PATENT DOCUMENTS

| | | | |
|---|---|---|---|
| 5,709,683 A * | 1/1998 | Bagby | ........................ A61F 2/44 623/16.11 |
| 7,063,701 B2 | 6/2006 | Michelson | |
| 7,281,925 B2 * | 10/2007 | Hall | ..................... A61C 8/0022 411/411 |
| 7,416,553 B2 | 8/2008 | Patel et al. | |
| 7,604,638 B2 | 10/2009 | Jacene et al. | |
| 7,776,047 B2 | 8/2010 | Fanger et al. | |
| 7,892,265 B2 * | 2/2011 | Perez-Cruet | ....... A61B 17/7025 606/300 |
| 7,909,829 B2 | 3/2011 | Patel et al. | |
| 7,909,848 B2 | 3/2011 | Patel et al. | |
| 7,914,561 B2 | 3/2011 | Konieczynski et al. | |
| 7,931,678 B2 | 4/2011 | Gorhan et al. | |
| 7,935,123 B2 | 5/2011 | Fanger et al. | |
| 7,935,137 B2 | 5/2011 | Gorhan et al. | |
| 8,298,271 B2 | 10/2012 | Jacene et al. | |
| 8,337,497 B2 | 12/2012 | DesLauriers et al. | |
| 8,394,107 B2 | 3/2013 | Fanger et al. | |
| 8,460,348 B2 | 6/2013 | Gorhan et al. | |
| 8,608,746 B2 | 12/2013 | Kolb et al. | |
| 8,668,697 B2 | 3/2014 | DesLauriers et al. | |

(Continued)

*Primary Examiner* — David W Bates
*Assistant Examiner* — Marcela I Shirsat
(74) *Attorney, Agent, or Firm* — O'Shea Getz P.C.

(57) ABSTRACT

A bone screw includes a main body having a proximal end and a distal end. The main body extends along a longitudinal axis. The main body has an externally threaded surface that includes at least one helically extending thread having a minor diameter and a major diameter, which major diameter is greater than the minor diameter. The thread includes at least two flank surfaces extending between the minor diameter and the major diameter. The minor diameter of the thread defines a central portion of the main body. The thread may include at least one aperture that extends along an aperture axis through the thread between the flank surfaces.

14 Claims, 10 Drawing Sheets

(56) References Cited

U.S. PATENT DOCUMENTS

| | | |
|---|---|---|
| 8,709,015 B2 | 4/2014 | Kolb et al. |
| 8,747,441 B2 | 6/2014 | Konieczynski et al. |
| 8,900,279 B2 | 12/2014 | Assell et al. |
| 8,940,025 B2 | 1/2015 | Konieczynski et al. |
| 2004/0028499 A1* | 2/2004 | Levey .................... F16B 33/02 411/112 |
| 2012/0197311 A1* | 8/2012 | Kirschman ........ A61B 17/7064 606/304 |
| 2015/0094764 A1 | 4/2015 | Konieczynski et al. |

* cited by examiner

BONE SCREW WITH APERTURES

The present application is entitled to the benefit of and incorporates by reference essential subject matter disclosed in U.S. Provisional Patent Application Ser. No. 61/986,602, filed Apr. 30, 2014.

BACKGROUND OF THE INVENTION

1. Field of Invention

The present invention relates generally to surgical implants, and more specifically to a bone screw with features that permit bone ingrowth.

2. Background Information

Fasteners are used in a variety of surgical applications including affixing implants to tissue and affixing tissue to tissue. A common surgical fastener is a bone screw, Which comprises threads designed to achieve mechanical purchase within bone. Bone screws exist in a variety of styles including pedicle screws, fracture fixation screws, and screws for securing bone plates. Bone screws are widely used because they are easy to insert, easy to produce, and under certain conditions provide adequate mechanical purchase. However, in applications involving highly porous, osteopenic or osteoporotic bone the efficacy of bone screws is substantially reduced. Design optimization of bone screws for these applications is challenged by competing constraints; the need for larger (i.e. coarser) threads versus the need for adequate bending strength (e.g., provided by the minor diameter of a screw) versus the maximally allowable major diameter (often limited by anatomy or mating component geometry). Further, bone screws function in a dynamic biological environment in which the supporting bone and tissue undergoes constant remodeling which can adversely affect the stability of the bone screw through time.

Design features aimed at improving the efficacy of bone screws without affecting the conventional thread form have focused on enhancing the implant-bone interface. Proposed enhancement have included use of biologically favorable metals (e.g. titanium), application of favorable coatings (e.g. hydroxyapatite), and surface texturing.

Other design solutions departing from conventional thread forms have incorporated features including expanding tips, trabecular metal, etc. These solutions may compromise the mechanical integrity of the screw.

Despite these proposed solutions, screw failure (e.g. loosening, breaking) is still a frequent clinical occurrence. Thus, the need exists for a bone fixation device that can be delivered as easily as a conventional bone screw, allows for bone ingrowth, and maintains adequate mechanical performance (e.g., pullout, bending).

SUMMARY

According to an aspect of the present disclosure, a bone screw is provided that includes a main body having a proximal end and a distal end, which main body extends along a longitudinal axis. The main body has an externally threaded surface that includes at least one helically extending thread having a minor diameter and a major diameter, which major diameter is greater than the minor diameter. The thread includes at least two flank surfaces extending between the minor diameter and the major diameter. The minor diameter of the thread defines a central portion of the main body. The thread includes at least one aperture that extends along an aperture axis through the thread between the flank surfaces.

According to another aspect of the present disclosure, a bone screw is provided that includes a main body having a proximal end and a distal end, which main body extends along a longitudinal axis. The main body has an externally threaded surface that includes at least one helically extending thread having a minor diameter and a major diameter, which major diameter is greater than the minor diameter. The thread includes at least two flank surfaces extending between the minor diameter and the major diameter. The minor diameter of the thread defines a central portion of the main body. The thread includes at least one recess disposed within one of the flank surfaces.

According to another aspect of the present invention, a bone screw is provided that includes a main body having a proximal end and a distal end, which main body extends along a longitudinal axis. The main body has an externally threaded surface that includes at least one helically extending thread having a minor diameter and a major diameter, which major diameter is greater than the minor diameter. The thread includes at least two flank surfaces extending between the minor diameter and the major diameter. The minor diameter of the thread defines a central portion of the main body, and the central portion includes a porous material.

The various bone screw embodiments described herein can be used for a variety of surgical applications including use as pedicle screws and fracture fixation screws.

In certain of the disclosed embodiments the apertures provide space into which bone can grow. In other embodiments the apertures define a structure that allows the threads to locally deform and accommodate local changes in bone density. In other embodiments the apertures accommodate an insert formed of an osteoconductive, osteoinductive or osteogenic material.

DETAILED DESCRIPTION

Figure 1:
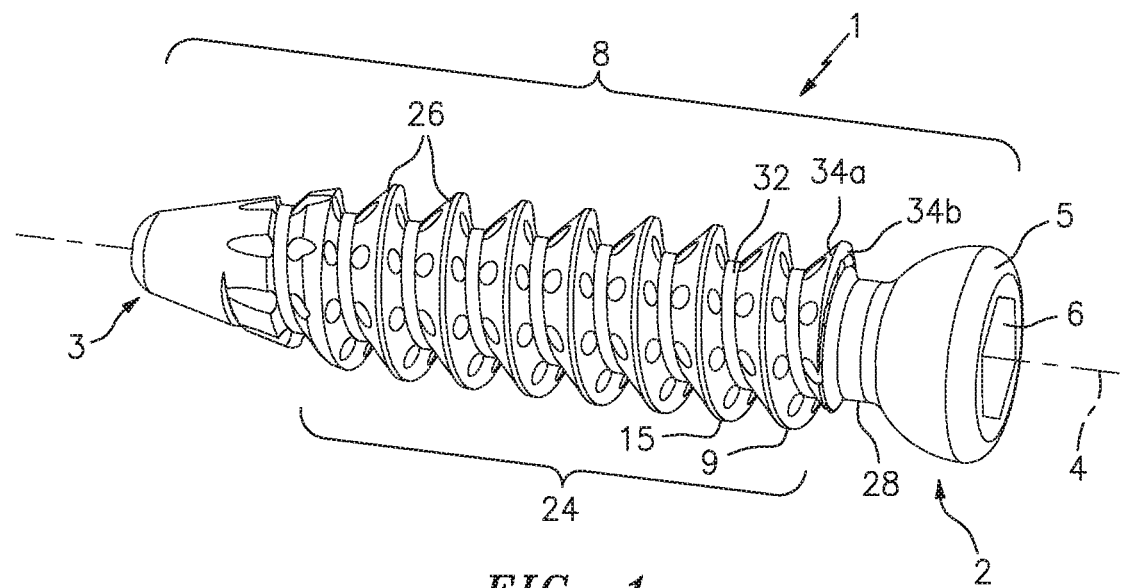
FIG. 1 is a perspective view of a bone screw embodiment.
Figure 2:
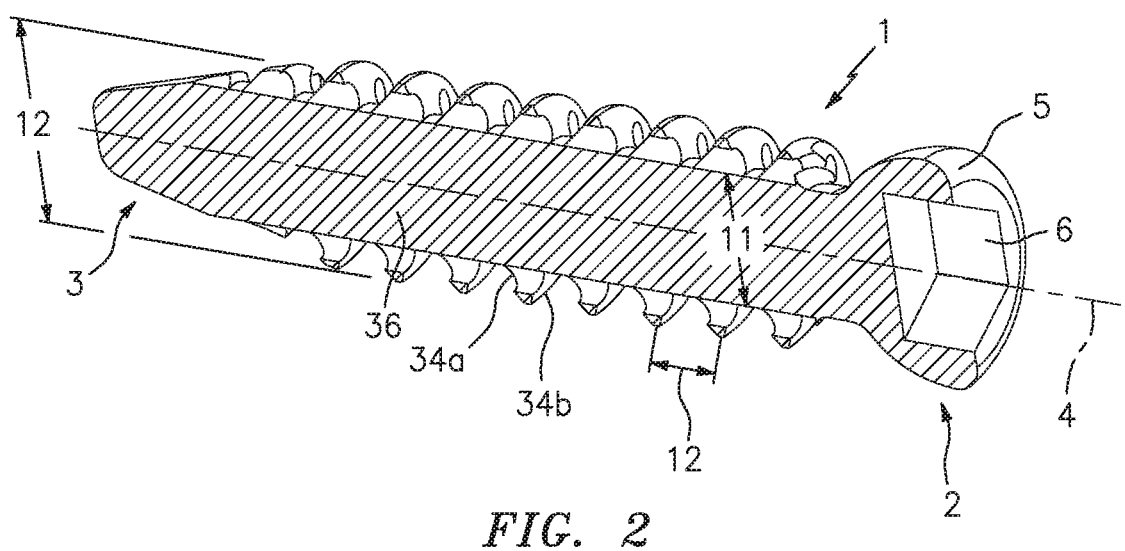
FIG. 2 is a cross-sectional view of the embodiment in FIG. 1.

Referring to FIG. 1, a bone screw 1 according to the present disclosure includes a main body 22 having a proximal end 2 and a distal end 3. A longitudinal axis 4 extends between the proximal end 2 and the distal end 3. The main body 22 includes an externally threaded surface 24 disposed between the proximal end and the distal end, which externally threaded surface 24 includes at least one helically extending thread 9 as will be described below.

The bone screw 1 may include a head 5 that is configured to allow the bone screw 1 to be rotationally driven (e.g., into a bone substrate). The present disclosure is not limited to any particular head configuration, and acceptable examples include a head 5 that can be driven by a screw driver, and hex key, etc. The bone screw head 5 may also be configured to mate with a complimentary element such as those used within bone fixation devices (e.g., a pedicle screw), plates, etc. The embodiment shown in FIG. 1, for example, includes a recess 6 configured to receive a hex key driver.

The portion of the main body 8 that includes the externally threaded surface 24 may be cylindrically-shaped; i.e., the major diameter of the thread 9 disposed within the threaded surface 24 (described below) is constant throughout substantially all the externally threaded surface 24 as is shown in FIGS. 1-10. The present disclosure is not limited to having a cylindrically-shaped externally threaded surface 24, however; e.g., the externally threaded surface 24 may be tapered.

The main body 8 may include a tip portion 7 contiguous with the distal end 3, which tip portion 7 is configured to facilitate entry of the bone screw 1 into a substrate (e.g., bone). Non-limiting examples of a tip portion 7 configured to facilitate entry of the bone screw 1 into a substrate (e.g., bone) include a tip portion 7 having a tapered region (i.e., a region that decreases from a first diameter to a smaller second diameter located at the distal end 3), which tapered region may be threaded, a tip portion having a self-tapping feature, or a tip portion having a self-drilling feature, or combinations thereof.

In some embodiments the bone screw 1 may include a shank portion 28 disposed between the proximal end 2 and the externally threaded surface 24.

The externally threaded surface 24 includes at least one helically extending thread 9 having a minor diameter 11 and a major diameter 12, which major diameter 12 is greater than the minor diameter 11. The major diameter 12 is disposed at the outer most radial point of the thread 9, and the minor diameter 11 is disposed at the inner most radial point of the thread 9. The outer most radial point of the thread 9 may be referred to as a "peak 15" of the thread 9, and the inner most radial point of the thread 9 may be referred to as a "root 32" of the thread 9. In those embodiments wherein the externally threaded surface 24 is cylindrically-shaped, an imaginary line drawn to intersect with the major diameter points of the helical thread 9 is parallel with the longitudinal axis 4 of the bone screw 1. In those embodiments wherein the externally threaded surface 24 is tapered, an imaginary line drawn to intersect with the major diameter points of the helical thread 9 is non-parallel with the longitudinal axis 4 of the bone screw 1. The thread 4 is further defined by at least two flank surfaces 34a, 34b extending between the minor diameter 11 and the major diameter 12, which flank surfaces 34a, 34b are disposed on opposite sides of the thread 9. The minor diameter 11 of the externally threaded surface 24 defines a central portion 36 of the main body 8.

The cross-sectional geometry of the helical thread 9 may be defined by parameters such as the major and minor diameters 11, 12, the flank surfaces 34a, 34b, shape, and the pitch 12 of the helical thread 9. In regards to the "shape" of the thread 9, the cross-sectional geometry of the thread 9 may reflect, for example, a symmetrical thread 9 having flank surfaces 34a, 34b, each disposed at the same angle relative to the longitudinal axis 4, or flank surfaces 34a, 34b disposed at different angles, etc. As another example, the flank surfaces 34a, 34b may intersect one another at the thread peak 15 (to form a pointed thread peak 15, or may not intersect one another (e.g., a truncated thread peak 15). The present disclosure is not limited to any particular thread cross-sectional geometry.

The particular cross-sectional geometry of the helical thread 9 may be selected in view of the application. For example, one embodiment of the present bone screw 1 may have a helical thread 9 with a cross-sectional geometry that is well-suited for mechanical engagement with a first type of substrate (e.g., porous bone, osteopenic bone, osteoporotic bone, etc.), while another embodiment of the present bone screw 1 may have a helical thread 9 with a cross-sectional geometry that is well-suited for mechanical engagement with a second type of substrate (e.g., dense bone, etc.). Embodiments of the present bone screw 1 may include more than one type of helical thread 9, or a helical thread 9 that has a plurality of cross-sectional geometries, each located at a different position.

To facilitate the description of the present disclosure, the various bone screw embodiments depicted in the drawings are shown as having single-lead right-handed threads 9. The present disclosure is not limited to bone screws 1 having a single-lead right-handed thread 9. For example, embodiments of the present bone screw 1 may have a left-handed thread 9 and/or multiple lead threads 9.

Figure 11:
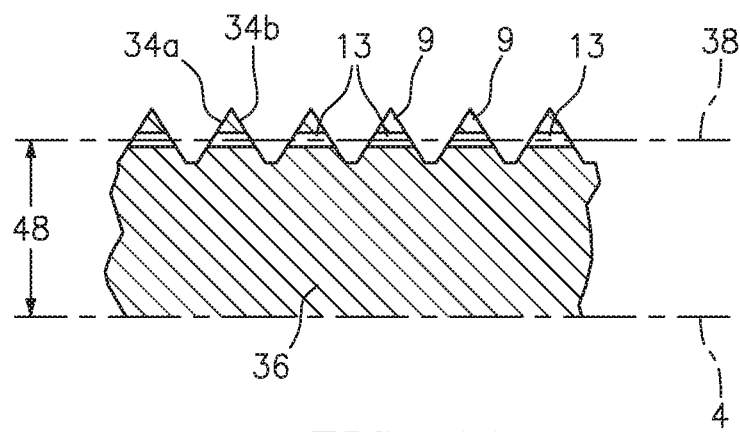
FIG. 11 is a diagrammatic sectional view of a threaded section portion.
Figure 11A:
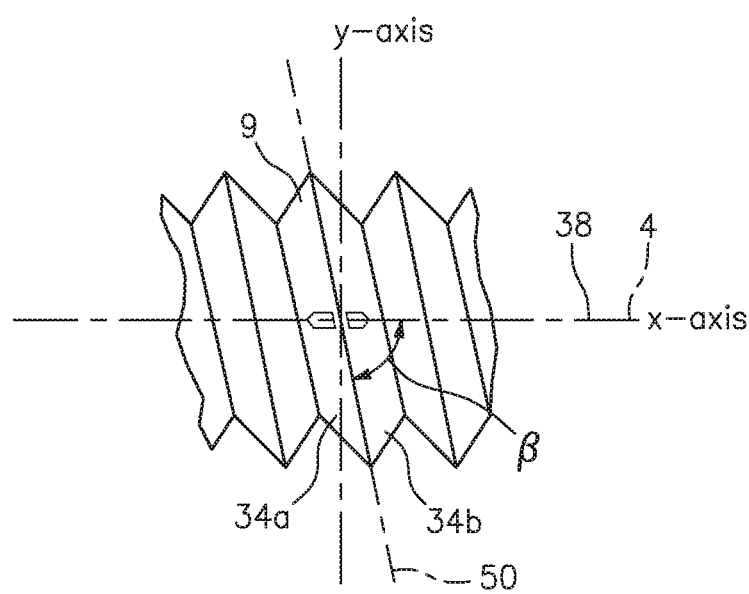
FIG. 11A is a diagrammatic planar view of a threaded section portion.

In some embodiments of the present bone screw 1, the helically extending thread 9 includes at least one aperture 13 extending through the thread 9. The aperture(s) 13 extends along an aperture axis 38 through the thread 9, from flank surface 34a to flank surface 34b of the thread 9 thereby providing an open passage through the body of the thread 9. The present bone screw is limited to any particular orientation of the aperture axis 38 (e.g., relative to the longitudinal axis 4). To illustrate a couple of exemplary aperture axis orientations, consider the present bone screw in terms of a pair of orthogonal axes X and Y. Consider further that the longitudinal axis 4 is coincident with the X axis, and the Y axis extends radially outward from the X-axis. Referring to FIGS. 11 and 11A, a first aperture axis 38 may be described as extending along a line parallel to the longitudinal axis 4 (i.e., parallel to the X-axis) at a particular distance front the longitudinal axis 4 (i.e., at a radial distance 48 out from the centrally located longitudinal axis 4—see FIG. 11). FIG. 11A shows axis 38 and axis 4 as the same because they are in the same radial plane. In FIG. 11A the radial distance 48 between axis 38 and axis 4 extends perpendicular (i.e., into) the 2-dimensional plane of the figure, and is therefore not shown. At the radial distance 48, the aperture axis 38 (and therefore the aperture 13) passes through the flank surfaces 34a, 34b of the thread 9. In this example, because the aperture axis 38 is parallel with the longitudinal axis 4, the aperture axis 38 is skewed by an angle (i.e., the aperture axis 38 is non-perpendicular) to the centerline 50 of the helically extending thread 9.

Figure 12:
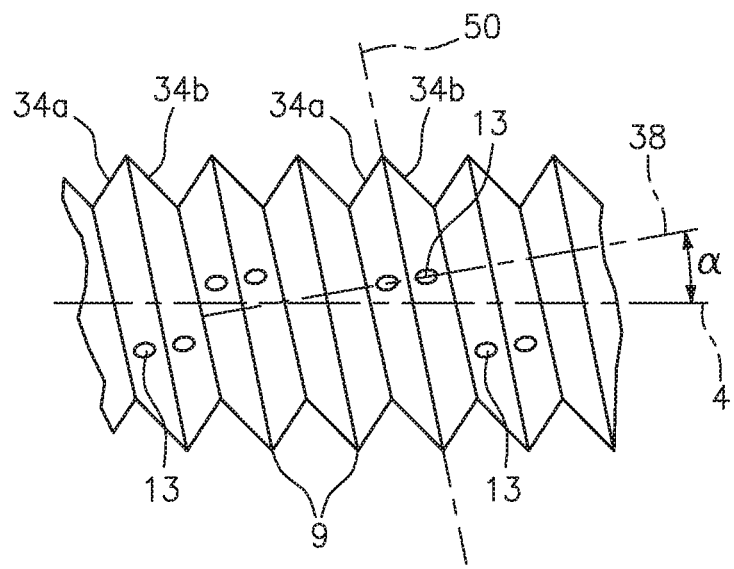
FIG. 12 is a diagrammatic planar view of a threaded section portion.

Now referring to FIG. 12, a second aperture axis example may be described as extending along a line skewed from the longitudinal axis 4 at a particular distance from the longitudinal axis 4 (i.e., at a radial distance 48 (e.g., see FIG. 11) out from the centrally located longitudinal axis 4). Here again, at the radial distance the aperture axis 38 (and therefore the aperture 13) passes through the flank surfaces 34a, 34b of the thread. In this example, the aperture axis 38 is skewed from the longitudinal axis 4 by an angle α which orients the aperture axis 38 as perpendicular to the centerline 50 of the helically extending thread 9.

In some embodiments, the apertures 13 are disposed completely within the thread(s) 9, and therefore do not extend radially inward of the minor diameter 11 of the threaded surface portion 24 (i.e., no portion of an aperture 13 is disposed within the central portion 36). In these embodiments because the entirety of the central portion 36 is maintained, the mechanical properties (e.g., bending strength) of the bone screw 1 are not locally compromised by an aperture 13 traversing the cylindrical central portion 36 defined by the minor diameter 11. In some embodiments, one or more apertures 13 may extend radially inside of the minor diameter 11 and therefore into the central portion 36 of the threaded surface portion 24 of the bone screw 1 (i.e., a portion of an aperture 13 is disposed within the central portion 36).

FIGS. 1-10 depict bone screw 1 embodiments having apertures 13 disposed within the helical thread 9 over substantially the entire externally threaded surface portion 24. In alternate embodiments the apertures 13 may be disposed within the helical thread 9 within less than the entirety of the externally threaded surface portion 24. For example, in some embodiments a portion of the helical thread 9 disposed adjacent the head 5 may not include apertures 13. The specific placement of the apertures 13 can be chosen to customize the bone screw 1 for the application at hand; e.g., positioning the apertures 13 to provide increased or decreased strength or deflection thread zones, zones where more bone affixation is desired, zones where inserts 618 (described below) are desired, etc.

In some embodiments (e.g., see FIGS. 1 and 2), the apertures 13 are circular shaped cross-sectional area. The circular apertures 13 are not limited to any particular diameter. For example, in many applications a bone screw 1 having circular apertures 13 with a diameter of approximately 1-2 mm is useful. The circular apertures 13 may, however, have smaller or larger diameters, or combinations thereof. The range of acceptable aperture diameters is bounded by the minimum feature size into which new bone would grow (~100 microns) and a maximum feature size that provides adequate fastener bending strength.

Figure 3:
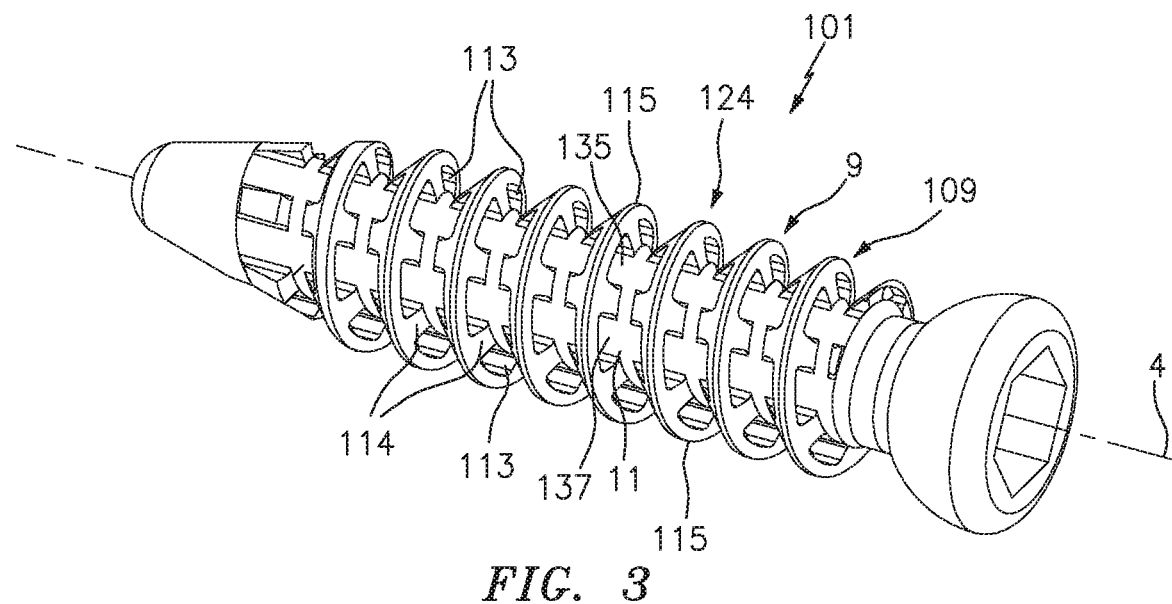
FIG. 3 is a perspective view of a bone screw embodiment.
Figure 3A:
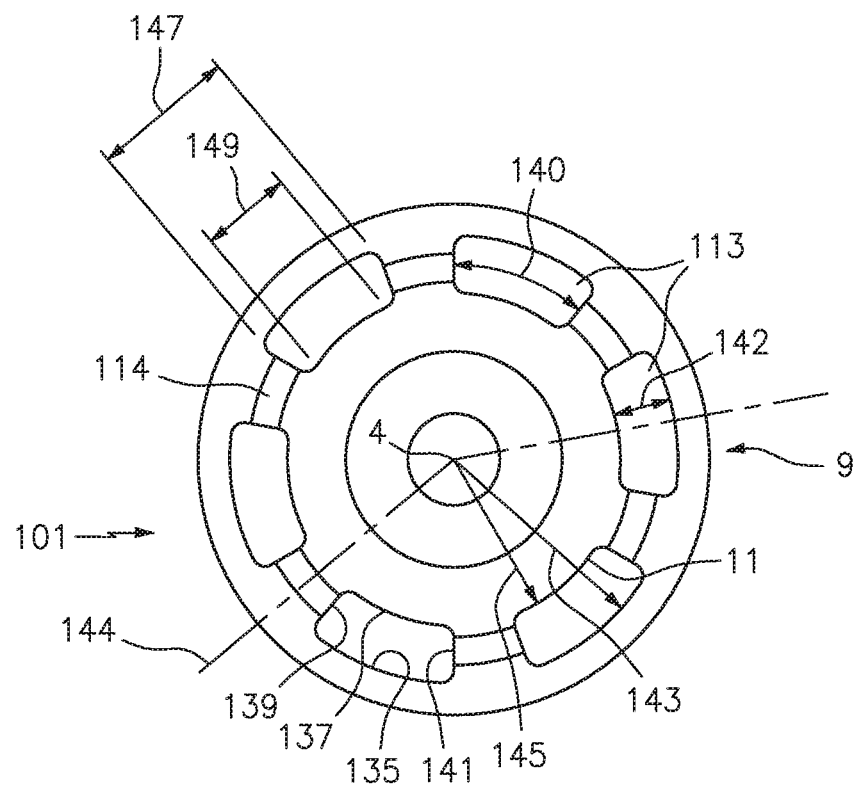
FIG. 3A is a distal end view of the bone screw embodiment shown in FIG. 3.

Referring to FIGS. 3 and 3A, in another embodiment the apertures 113 of bone screw 101 have a substantially trapezoidal shape. Each trapezoidal shaped aperture 113 is defined by an outer radial surface 135, an inner radial surface 137, a first lateral surface 139, and a second lateral surface 141, and has a circumferentially extending width 140 and a radially extending height 142 (e.g., see FIG. 3A). As can be seen in FIG. 3A, for example, the outer radial surface 135 extends circumferentially at a first radial distance 143 from the longitudinal axis 4, and the inner radial surface 137 extends circumferentially at a second radial distance 145 from the longitudinal axis 4. The first radial distance 143 is greater than the second radial distance 145; i.e., the difference between the first radial distance 143 and the second radial distance 145 is the height 142 of the aperture 113. In the embodiment shown in FIGS. 3 and 3A (as well as those shown in FIGS. 4-7A), the inner radial surface 137 of the aperture 113 is coincident with the minor diameter 11 of the respective thread 9. The outer radial surface 135 extends a first circumferential distance 147 between the first lateral surface 139 and the second lateral surface 141, and the inner radial surface 137 extends a second circumferential distance 149 between the first lateral surface 139 and the second lateral surface 141. The first circumferential distance 147 is greater than the second circumferential distance 149. The trapezoidal aperture 113 configuration shown in FIG. 3 has a width 140 greater than a height 142, thereby providing apertures 113 with a greater cross-sectional area as compared to the circular apertures 13 depicted in FIGS. 1 and 2. Here apertures 113 are arranged circumferentially about the bone screw, with adjacent apertures 113 circumferentially separated from one another by a thread portion hereinafter referred to as a strut 114. The struts 114 function to provide support for the thread peak 115, which in this embodiment runs relatively uninterrupted along the threads 109 and over the full length of the threaded surface 124. The strut 114 has a centerline 144. In some embodiments, a strut 114 may have a centerline 144 that extends along a line that extends radially outward from the longitudinal axis 4 (e.g., see FIG. 3A). In some embodiments, a strut 414 may have a centerline 444 that extends along a line that extends at an angle skewed from a radial line extending outward from the longitudinal axis 4 (e.g., see FIG. 6A). In certain embodiments a relatively uninterrupted thread peak 115 is advantageous in that it provides a smooth bone contacting surface that facilitates insertion of the bone screw 101. In this embodiment the apertures 113 extending longitudinally along the length of the main body 8 are coaxial to one another. In an alternate embodiment the apertures 113 are not positioned in a coaxial fashion, but rather staggered such that when viewed on end an unobstructed line of sight through all the apertures 113 is not possible.

Figure 4:
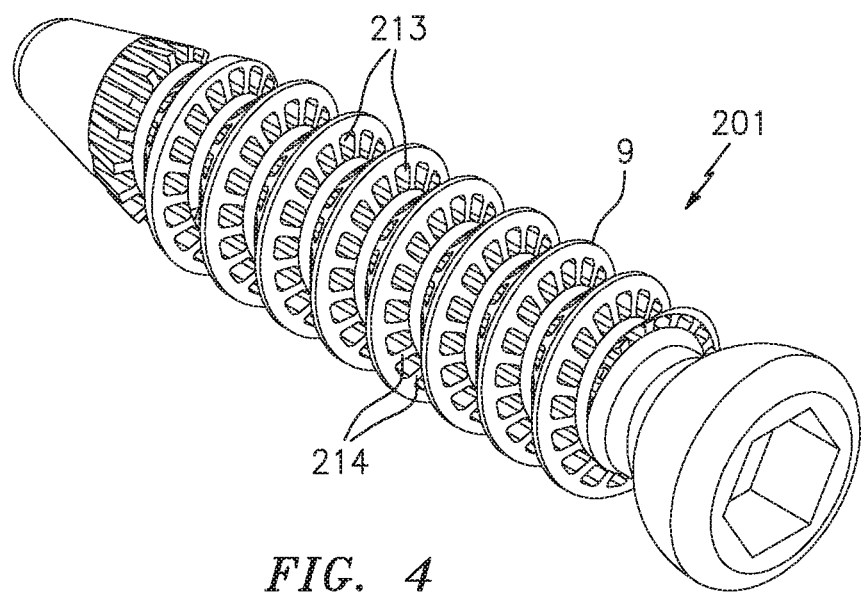
FIG. 4 is a perspective view of a bone screw embodiment.
Figure 4A:
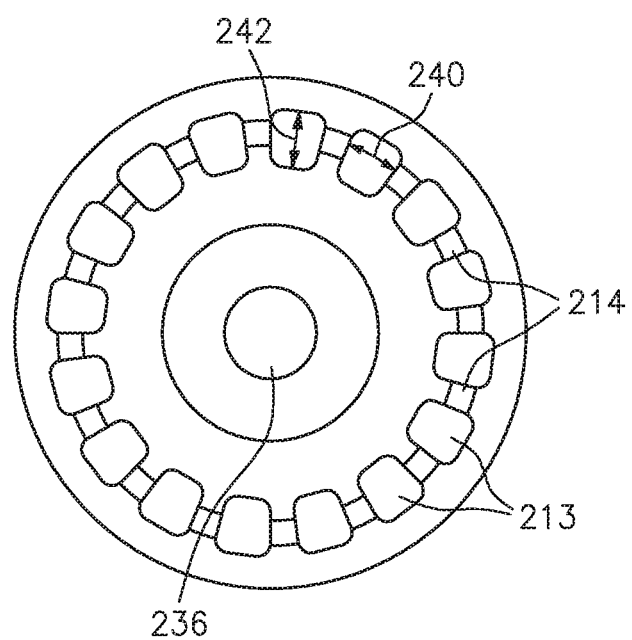
FIG. 4A is a distal end view of the bone screw embodiment shown in FIG. 4.

The embodiment shown in FIGS. 4 and 4A has substantially trapezoidal-shaped apertures 213, each having outer radial surface, an inner radial surface, a first lateral surface, and a second lateral surface, arranged in the manner described above with respect to the embodiment shown in FIGS. 3 and 3A. In contrast to the embodiment shown in FIGS. 3 and 3A, the apertures 213 shown in the embodiments depicted in FIGS. 4 and 4A each have a circumferentially extending a width 240 less than a radially extending height 242, thereby providing apertures 213 with a smaller cross-sectional area. In this configuration, the size and number of apertures 213 relative to the struts 214 provide a relatively stiff thread peak 215. The central portion 236 is shown in FIG. 4A.

Figure 5:
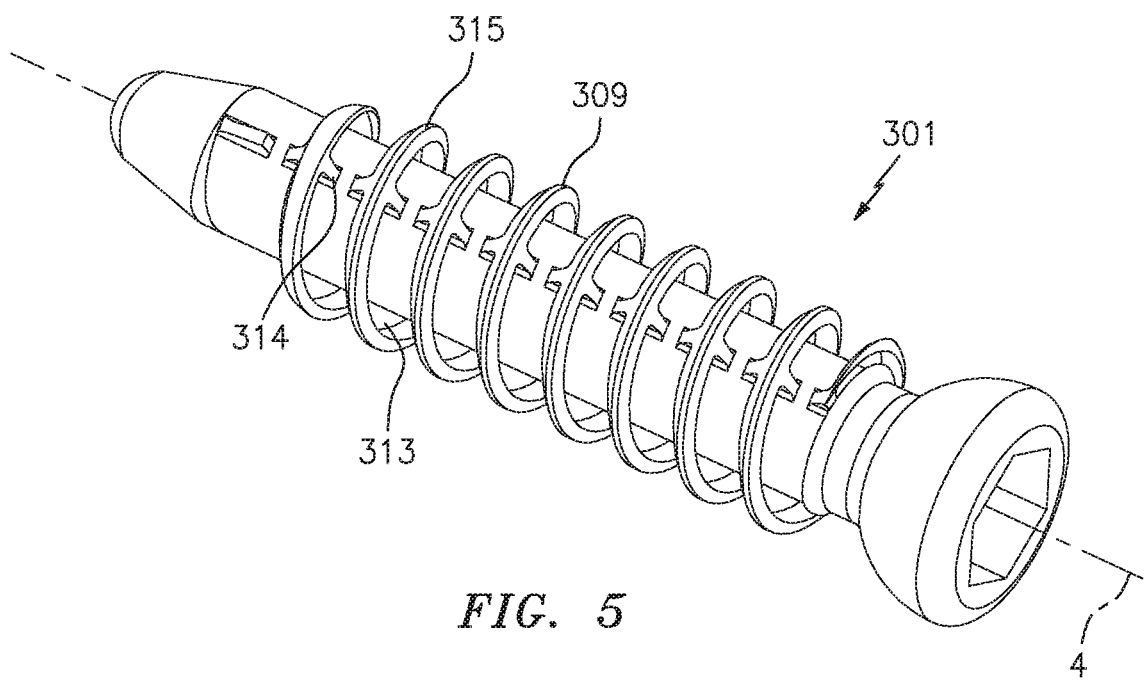
FIG. 5 is a perspective view of a bone screw embodiment.
Figure 5A:
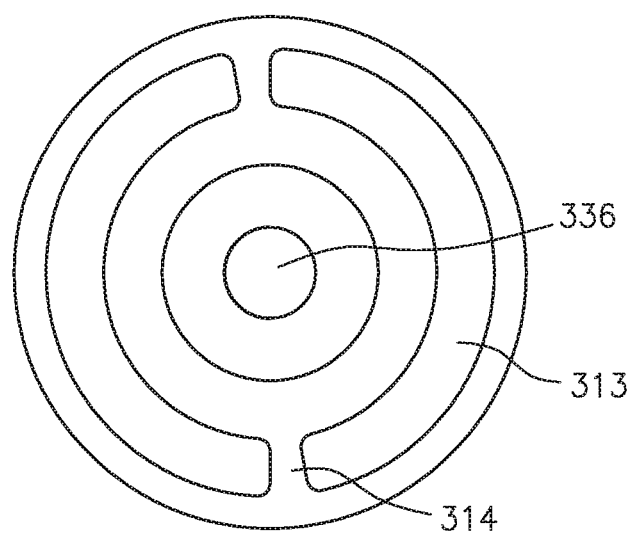
FIG. 5A is a distal end view of the bone screw embodiment shown in FIG. 5.

FIGS. 5 and 5A depict a bone screw 301 embodiment in which the apertures 313 have a greater cross-sectional area than the apertures 113 shown in FIG. 3; e.g., semi-annular shaped apertures. Here the size and number of apertures 313 relative to struts 314 provides relatively more volume into which bone can grow. In certain embodiments there may be less than one strut per revolution of the helical thread 309.

Still referring to FIGS. 5 and 5A, the individual aperture size (i.e., the cross-sectional area) and total number of apertures 313 results in a relatively flexible thread peak 315. The flexible thread peak 315 is advantageous in that during insertion of the bone screw 301 fastener it can locally deflect to accommodate the geometry of the space it is filling. For example, if the bone into which the bone screw 301 is being inserted has a localized region of greater bone density, the flexible thread peak 315 can elastically deforms as it passes that region. After passing that region, the flexible thread peak 315 elastically returns to its nominal undeformed state. In this way the bone screw 301 is affixed to bone of non-homogeneous density and/or structure. In certain applications it may be permissible or even advantageous for the flexible thread peak 315 to plastically deform. The central portion 336 is shown in FIG. 5A.

Figure 6:
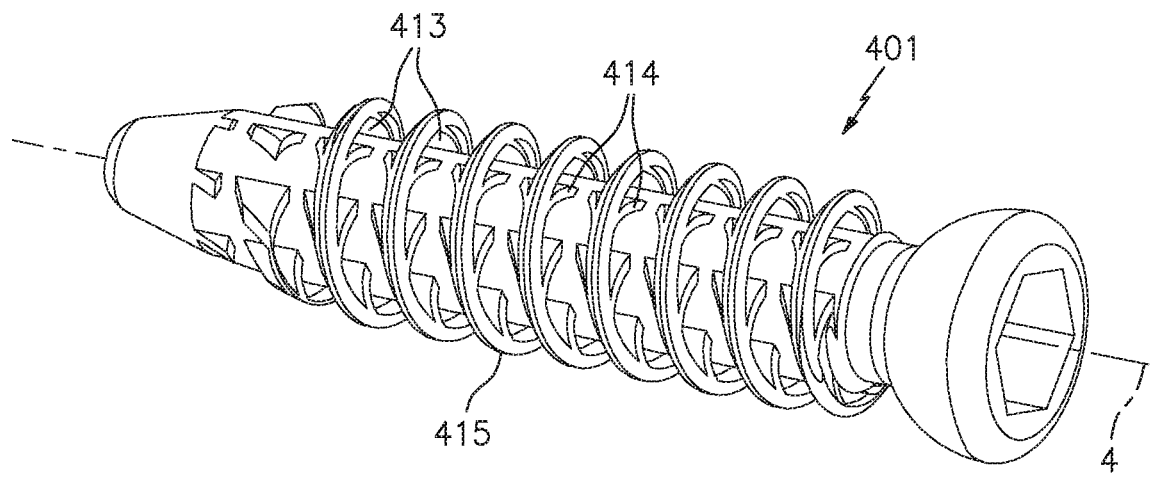
FIG. 6 is a perspective view of a bone screw embodiment.
Figure 6A:
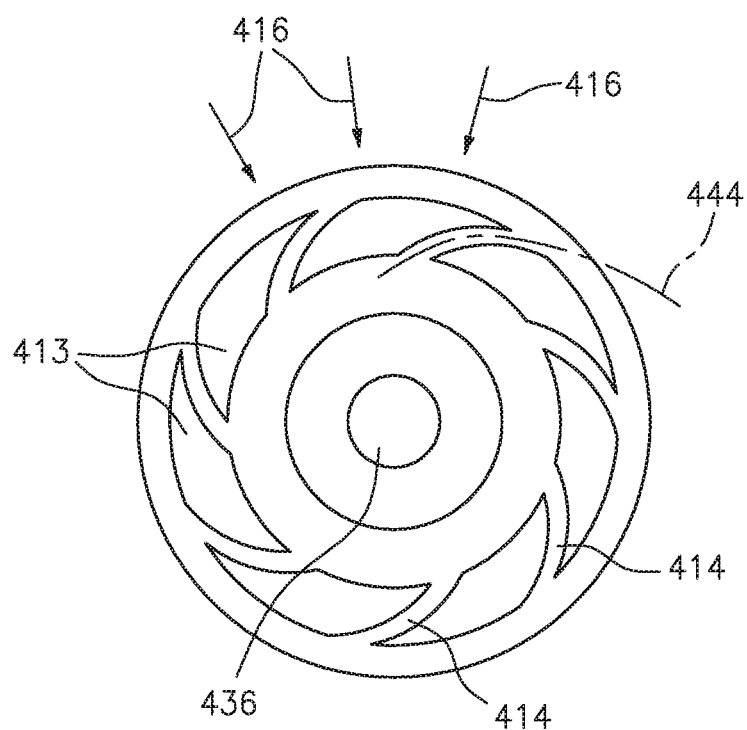
FIG. 6A is a distal end view of the bone screw embodiment shown in FIG. 6.

Now referring to FIGS. 6 and 6A, in some embodiments, the apertures 413 of bone screw 401 are shaped such that adjacent apertures 413 form struts 414 favorably oriented to accommodate deformation of the flexible thread peak 415. For example, as can be seen in FIG. 6A, adjacent apertures 413 can be configured to form struts 414 that extend at an angle skewed from a radial line extending out from the longitudinal axis. In this configuration, under locally applied radial forces 416 the struts 414 are primarily subject to bending forces rather than compressive forces, allowing greater plastic deformation of the flexible thread peak 415.

Figure 7:
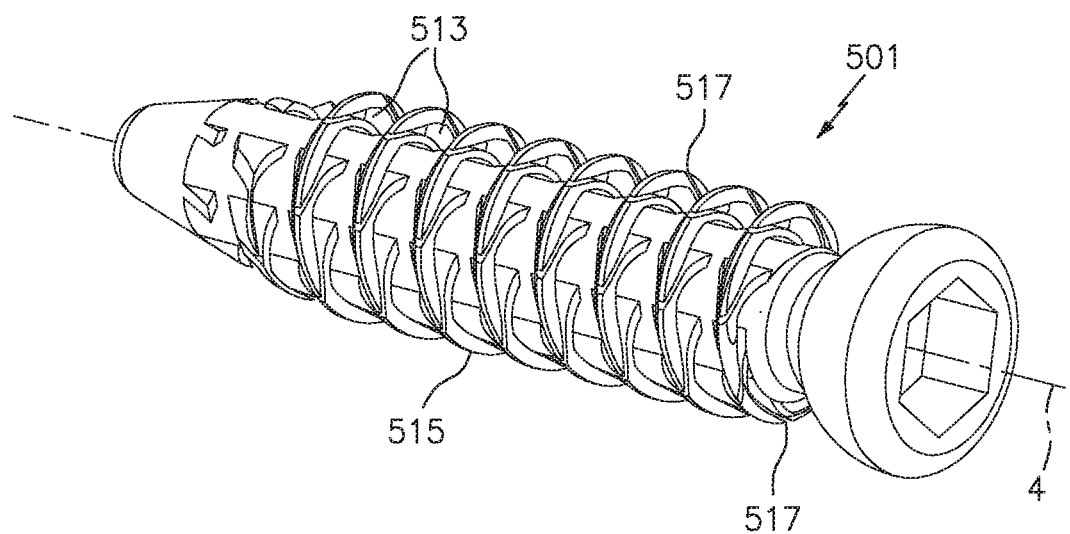
FIG. 7 is a perspective view of a bone screw embodiment.
Figure 7A:
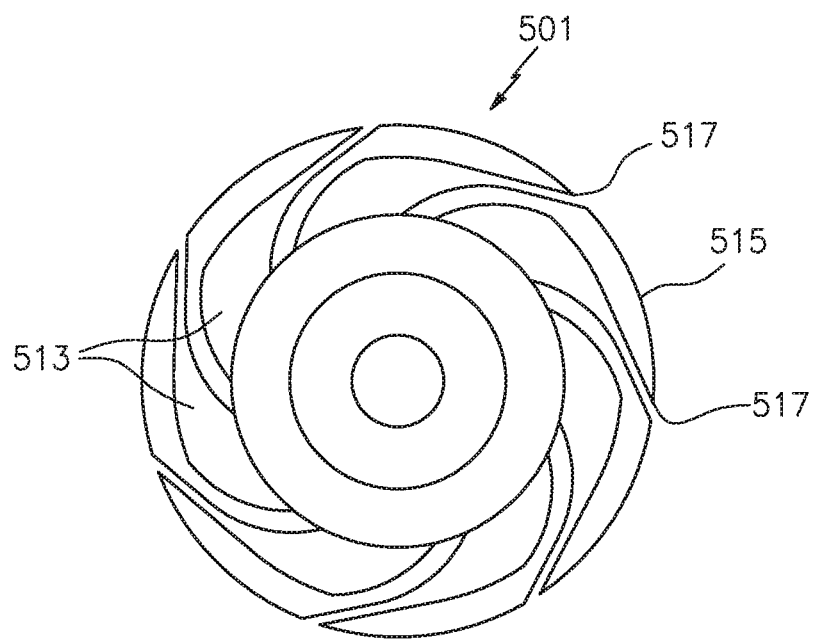
FIG. 7A is a distal end view of the bone screw embodiment shown in FIG. 7.

In some embodiments an aperture of bone screw may be defined by an "open geometry" or an "open perimeter"; i.e., the aperture breaks through the peak of the thread. For sake of clarity, an aperture having a "closed geometry" or a "closed perimeter" is one in which the circumferential perimeter of the aperture is continuous and therefore cannot be accessed through the peak of the thread. FIG. 7, for example, shows a bone screw 501 with apertures 513 having slits 517 that interrupt the flexible thread peak 515 and allow portions of flexible thread peak 515 to deform relatively independently of other portions of the flexible thread peak 515. The slits 517 can be relatively thin, and in certain embodiments provide physical contact or near contact between adjacent portions of the flexible thread peak 515. In this way one portion of the flexible thread peak 515 provides displacement constraint for another portion of the flexible thread peak 515. In another embodiment, the slits 517 may be configured to allow the entirety of the flexible thread peak 515 to deform and achieve an effective smaller major diameter over the entire length of the shaft. When the bone screw 501 of this type having a diameter "X" is inserted into a hole with a diameter less than "X", the flexible thread peak deforms to create an effectively smaller major diameter. Once fully inserted, the flexible thread peak 515 provides a restorative radial force (i.e., a radially outward biasing force) that acts to enhance mechanical purchase.

Figure 8:
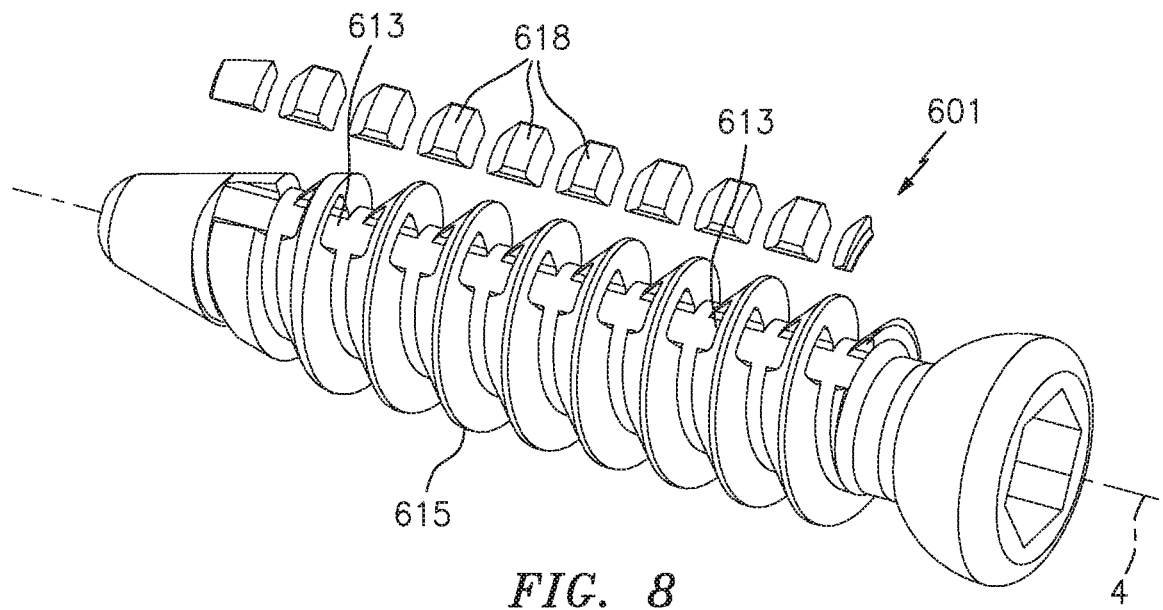
FIG. 8 is a perspective exploded view of a bone screw embodiment.
Figure 8A:
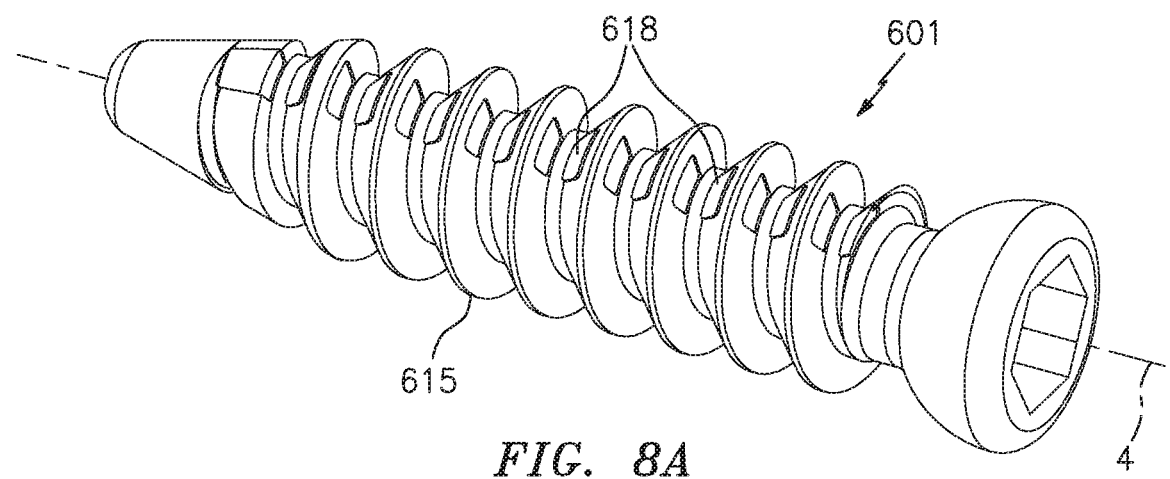
FIG. 8A is a perspective view of the bone screw embodiment with inserts disposed in the thread.

One function of the various aperture embodiments is to provide a volume into which bone can grow and form a mechanical interlock that resists fastener loosening. Referring to FIGS. 8 and 8A, in an alternate embodiment the apertures 613 of bone screw 601 may be filled with a material other than the material of which the bone screw 1 is comprised. The material disposed in the apertures is referred to hereinafter as an "insert 618". The present disclosure is not limited to any particular manner of disposing the inserts 618 within the apertures. For example, the inserts 618 may be affixed with the apertures 613 by the manufacturer of the bone screw 601. Alternately, the inserts 618 may be affixed to the bone screw at a time subsequent to the manufacture of the bone screw; e.g., at the time of surgery. As diagrammatically shown in FIG. 8, the inserts 618 may have a shape approximating the shape of the corresponding aperture 613. One or more nominal dimensions of the inserts 618 may be larger than the corresponding dimension of the apertures 613 such that the inserts 618 are affixed to the bone screw 601 via an interference fit. Alternately, the inserts 618 may be affixed using an adhesive or a mechanical interlock. In other embodiments the pre-insertion shape of the insert 618 does not approximate the shape of the aperture 613. For example, an amorphous volume of granular autograft material may be pressed into the apertures 613.

In some embodiments, the inserts 618 may be constructed to enhance the stability of the fastener within the bone, either immediately upon insertion or through time. The inserts 618 may be constructed from a variety of known materials that provide or carry osteoconductive, osteoinductive or osteogenic elements including but not limited to tricalcium phosphate, hydroxyapatite, bone morphogenic proteins, absorbable polymers, autograft, allograft, xenograft, and demineralized bone matrix. In some embodiments the inserts 618 may be constructed of materials that provide antimicrobial or antibacterial characteristics, including but not limited to drugs, silver, and bioglass. In some embodiments the insert 618 can be formed from an adhesive material, for example polyurethane bone cement. Upon insertion of the fastener, the adhesive adheres to both the bone screw 601 and the bone, thereby enhancing initial bone screw stability. In another embodiment the insert 618 expands upon insertion, filling voids within the bone and thereby enhancing initial bone screw stability. The present disclosure includes embodiments wherein all of the inserts 618 are the same material and/or configuration, and also embodiments where there are inserts 618 of a first type material and/or configuration, and other inserts of a different type material and/or configuration.

The embodiment shown in FIG. 8 comprises apertures 613 positioned at a single location along the perimeter of the shaft 608. In this and similar embodiments with fewer or smaller apertures the thread peak 615 is relatively inflexible. Here the thread peak 615 and other thread portions 609 act to protect the insert 618 from damage or displacement during fastener insertion.

Figure 9:
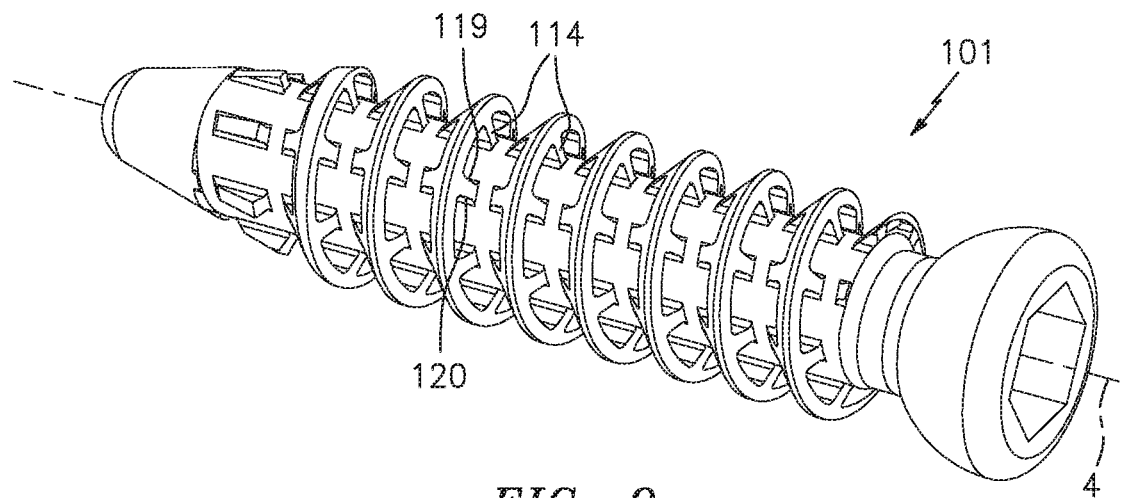
FIG. 9 is a perspective view of a bone screw embodiment.

Referring the FIG. 9, the struts 114 of bone screw 101 are comprised of leading edges 119 and trailing edges 120. During rotational insertion of the fastener, the leading edges 119 follow the apertures 113 and the trailing edges 120 follow the struts 114. In the embodiment shown in FIG. 9, both the leading edges 119 and trailing edges 120 of the struts 114 are configured with a sharp edge (e.g., a pointed edge formed by the respective strut surfaces intersecting at an approximately 90-degree corner), In some embodiments the leading edges 119 may be formed such that the respective strut surfaces intersect to form a rounded or chamfered edge that is less likely to catch or cut into adjacent bone. In some embodiments the trailing edges 120 may be formed to such that the respective strut surfaces intersect at an acute angle such that the trailing edge 120 is effective at cutting bone. In some embodiments, both the leading edges 119 and trailing edges 120 are formed by an acute angle within the strut 114 such that they are effective at cutting bone.

The specific aperture shape embodiments described above reflect some but not all of the aperture shapes contemplated by the present disclosure. Consequently, the present disclosure is not limited to any particular aperture shape, and is not limited to just those aperture shapes described above. In addition, a bone screw according to the present disclosure may include more than one type of bone screw apertures. For example, a first region of a bone screw 1 proximate the head 5 of the bone screw 1 may include one or more apertures 13 disposed within the helical thread 9 of a first type (e.g., a first shape), and a second region of a bone screw 1 proximate the tip 7 of the bone screw 1 may include one or more apertures 13 disposed within the helical thread 9 of a second type (e.g., a second shape). Using a second type of aperture 13 near the distal end 3 of the bone screw 1 where the tip 7 tapers and the thread major diameter 12 and minor diameter 11 vary can be beneficial. Hence, the present disclosure includes bone screw embodiments having a plurality of aperture types disposed at various positions along the externally threaded surface, interdispersed aperture types, etc.

Figure 13:
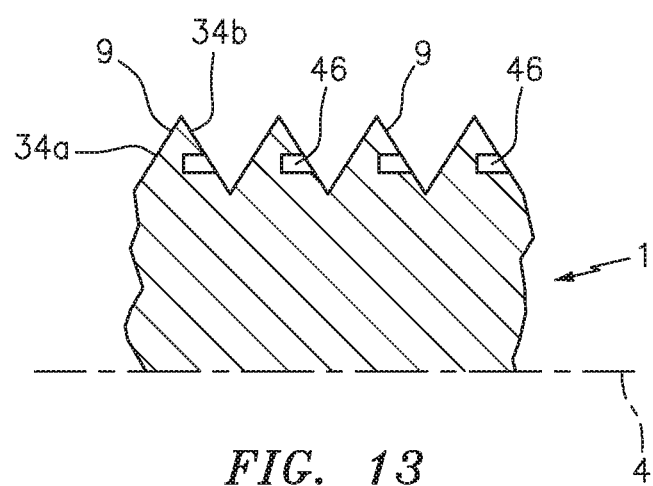
FIG. 13 is a diagrammatic sectional view of a threaded section portion.

Although the embodiments shown in the FIGS. 1-12 depict apertures (i.e. hole features that pass completely through the threads), alternate embodiments may include one or more recesses 46 disposed within a flank surface 34a, 34b of the helical thread 9 (e.g., see FIG. 13). A recess 46 may be defined as a void open at a flank surface 34a, 34b, that extends into the flank surface but does not extend entirely through the helical thread 9 (i.e., it does not extend between flank surfaces to create a passage through the helical thread 9). These recesses 46 are configured (e.g., depth, width, height, and/or geometry) such that once the bone screw 1 is inserted, over time bone (or other tissue) may extend into the recess 46 and thereby provide a mechanical interlock resisting screw loosening or backout. These recesses 46 may be oriented substantially parallel to the longitudinal axis 4 of the bone screw 1. In some embodiments of the present disclosure, the bone screw 1 may include both recesses 46 and apertures 13 disposed within the helical thread 9.

Figure 10:
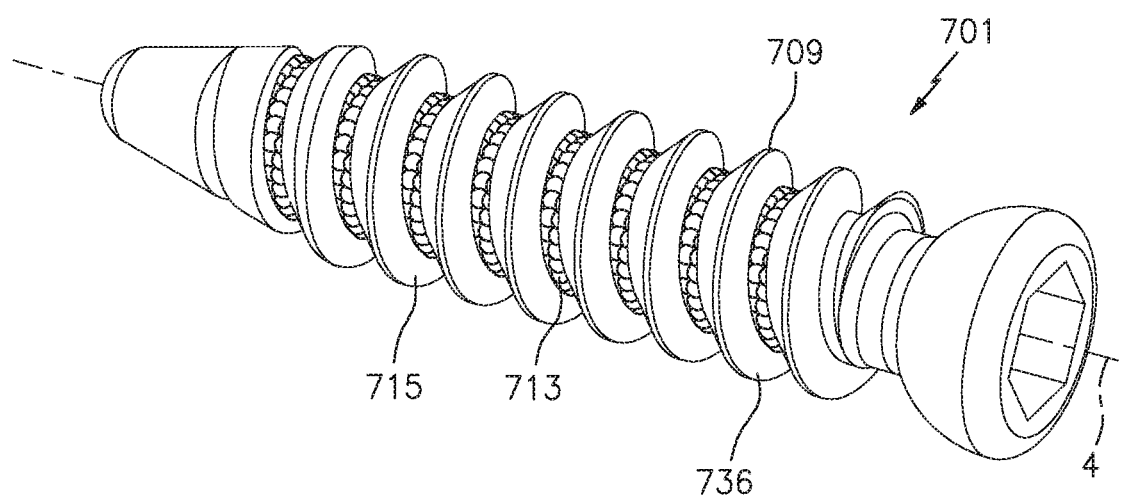
FIG. 10 is a perspective view of a bone screw embodiment.

Referring to FIG. 10, in another embodiment the central portion of the externally threaded surface includes an aperture network 713 that includes pathways that are oriented in multiple directions. For example, the central portion 736 (defined by the minor diameter) may include a porous structure favorable to bone growth into the pathways. Examples of an acceptable material that can be used to form a porous structure part of the central portion include, for example, Porocoat® coating (available from DePuy Synthes, Inc.) or Trabecular Metal™ surface technology (available from Zimmer, Inc.). The threads 709 that overlay this aperture network 713 may be formed from a substantially solid material. Thus, as the solid bone screw threads 709 engage a hole within a corresponding substrate (e.g., bone tissue), the threads 709 provide a smooth substrate contact surface that facilitates insertion. The aperture network 713, which is in less intimate contact with bone during insertion, provides later access for bone ingrowth. Also, the solid threads 709 enhance the rigidity and strength to the bone screw 701. In some embodiments the pathway network created by the porous structure is disposed in both a portion of the cylindrical region of shaft approximately bounded by the minor thread diameter and a portion of the threads. In this embodiment the thread peaks 715 are uninterrupted (i.e. without pores), providing a smooth bone interface surface.

Fabrication of the various embodiments may benefit from additive manufacturing techniques (i.e. 3D printing). However, the scope of invention is not limited to a specific manufacturing technology. Embodiments may be manufactured from stainless steel, cobalt chromium, titanium, polymers, ceramics and other suitable materials.

In one fabrication method the bone screw 1 is comprised wholly of a material provided by an additive manufacturing process; e.g., printing. In another fabrication method a portion of the bone screw 1 is formed by a first process comprising conventional manufacturing techniques (e.g. machining, casting, rolling, stamping) and a portion of the bone screw 1 is formed by a second process comprising additive manufacturing techniques. By way of example, in one embodiment the central portion 36 is formed using conventional manufacturing techniques and the thread 9 is formed using additive manufacturing techniques.

Lastly, although this present disclosure is described herein as a bone screw, the present disclosure device is not limited to bone screw applications. These applications include but are not limited to other medical applications (e.g. soft tissue anchors) and non-medical applications (e.g. screws for fastening wood, drywall and concrete).

Although the invention has been shown and described with respect to specific detailed embodiments thereof, it will be understood by those skilled in the art that various changes in form and detail thereof may be made without departing from the spirit and the scope of the invention.

What is claimed is:

1. A bone screw, comprising:
a main body having a proximal end and a distal end, which main body extends along a longitudinal axis;
the main body having an externally threaded surface that includes at least one helically extending thread having a minor diameter and a major diameter and a peak, the peak disposed at the major diameter, wherein the major diameter is greater than the minor diameter, and wherein the thread includes a first flank surface extending between the minor diameter and the major diameter and a second flank surface extending between the minor diameter and the major diameter, the first flank surface being disposed on the opposite side of the thread from the second flank surface;
wherein the minor diameter of the at least one helically extending thread defines a central portion of the main body; and
wherein the at least one helically extending thread includes at least one trapezoidal aperture that extends through the thread from the first flank surface to the second flank surface, the at least one aperture defined by an outer radial surface, an inner radial surface, a first lateral surface, and a second lateral surface, and the inner radial surface of the at least one aperture is coincident with the minor diameter of the at least one helically extending thread; and
wherein the outer radial surface of the at least one aperture is disposed radially inside of the major diameter, and the at least one aperture has a closed perimeter.

2. The bone screw of claim 1, wherein the externally threaded surface of the main body extends a length, and the at least one aperture includes a plurality of the apertures disposed in the thread at positions located throughout substantially all of the externally threaded surface length.

3. The bone screw of claim 1, wherein the outer radial surface extends a first circumferential distance between the first lateral surface and the second lateral surface, and the inner radial surface extends a second circumferential distance between the first lateral surface and the second lateral surface, and the first circumferential distance is greater than the second circumferential distance.

4. The bone screw of claim 1, wherein the at least one aperture includes a plurality of the apertures, wherein adjacent apertures are separated from one another within the thread by a strut portion of the thread.

5. The bone screw of claim 4 wherein the strut portion of the thread has a centerline that extends radially.

6. The bone screw of claim 1, wherein the externally threaded surface of the main body extends a length, and the at least one aperture includes a plurality of the apertures disposed in the at least one helically extending thread.

7. The bone screw of claim 1, wherein the first lateral surface and the second lateral surface converge toward one another traveling in a radially inward direction.

8. A bone screw, comprising:
- a main body having a proximal end and a distal end, which main body extends along a longitudinal axis;
- the main body having an externally threaded surface that includes at least one helically extending thread having a minor diameter and a major diameter, which major diameter is greater than the minor diameter, and which thread includes at least two flank surfaces extending between the minor diameter and the major diameter;
- wherein the minor diameter of the at least one helically extending thread defines a central portion of the main body; and
- wherein the at least one helically extending thread includes at least one aperture that extends through the thread between the flank surfaces, the at least one aperture defined by an outer radial surface, an inner radial surface, a first lateral surface, and a second lateral surface, and the inner radial surface of the at least one aperture is coincident with the minor diameter of the at least one helically extending thread; and
- wherein the outer radial surface extends a first circumferential distance between the first lateral surface and the second lateral surface, and the inner radial surface extends a second circumferential distance between the first lateral surface and the second lateral surface, and the first circumferential distance is greater than the second circumferential distance; and
- wherein the at least one aperture includes a height extending between the outer radial surface and the inner radial surface, the height is less than second circumferential distance.

9. The bone screw of claim 8 wherein the at least one aperture has a closed perimeter.

10. The bone screw of claim 8, wherein the externally threaded surface of the main body extends a length, and the at least one aperture includes a plurality of the apertures disposed in the at least one helically extending thread.

11. The bone screw of claim 10, wherein the plurality of the apertures are disposed in the thread at positions located throughout substantially all of the externally threaded surface length.

12. The bone screw of claim 8, wherein the at least one aperture includes a plurality of the apertures, wherein adjacent said apertures are separated from one another within the thread by a strut portion of the thread.

13. The bone screw of claim 12 wherein the strut portion of the thread has a centerline that extends radially.

14. The bone screw of claim 8, wherein the first lateral surface and the second lateral surface converge toward one another traveling in a radially inward direction.

* * * * *